(12) United States Patent
Zhang et al.

(10) Patent No.: US 12,349,952 B2
(45) Date of Patent: Jul. 8, 2025

(54) GRASPING INSTRUMENT, TRACKING AND NAVIGATION SYSTEM, METHOD AND DISPLAY APPARATUS, AND STORAGE MEDIUM

(71) Applicants: THE FOURTH MEDICAL CENTER OF PLA GENERAL HOSPITAL, Beijing (CN); Lei Hu, Beijing (CN)

(72) Inventors: Lihai Zhang, Beijing (CN); Lei Hu, Beijing (CN); Hailong Du, Beijing (CN); Gongzi Zhang, Beijing (CN); Ye Peng, Beijing (CN)

(73) Assignees: Lei Hu, Beijing (CN); THE FOURTH MEDICAL CENTER OF PLA GENERAL HOSPITAL, Beijing (CN)

( * ) Notice: Subject to any disclaimer, the term of this patent is extended or adjusted under 35 U.S.C. 154(b) by 189 days.

(21) Appl. No.: 18/249,819

(22) PCT Filed: Feb. 10, 2021

(86) PCT No.: PCT/CN2021/076581
§ 371 (c)(1),
(2) Date: Apr. 20, 2023

(87) PCT Pub. No.: WO2022/170586
PCT Pub. Date: Aug. 18, 2022

(65) Prior Publication Data
US 2024/0024011 A1  Jan. 25, 2024

(51) Int. Cl.
*A61B 17/88* (2006.01)
*A61B 34/20* (2016.01)

(52) U.S. Cl.
CPC .......... *A61B 17/8866* (2013.01); *A61B 34/20* (2016.02); *A61B 2034/2051* (2016.02)

(58) Field of Classification Search
CPC .................. A61B 17/8866; A61B 2034/2051
See application file for complete search history.

(56) References Cited

U.S. PATENT DOCUMENTS

| | | | |
|---|---|---|---|
| 2012/0201421 A1* | 8/2012 | Hartmann | A61B 6/5235 382/103 |
| 2013/0104672 A1* | 5/2013 | Kim | B25J 13/085 73/862.624 |
| 2020/0000530 A1* | 1/2020 | DeFonzo | A61B 34/37 |

FOREIGN PATENT DOCUMENTS

WO  WO 2017/040821  *  3/2017  ............. A61B 34/20

* cited by examiner

*Primary Examiner* — Christian A Sevilla
(74) *Attorney, Agent, or Firm* — Dorsey & Whitney LLP

(57) ABSTRACT

Provided are a grasping instrument, tracking and navigation system, method and display apparatus for bone structure reduction, and a storage medium. The grasping instrument includes a straight strip-shaped support rod, and a grasping end and a signal end that are arranged at two ends of the support rod; a plurality of grating sensors extending in an axial direction are arranged on the support rod; the signal end is provided with an instrument pose feedback sensor for feeding back pose information of the grasping instrument; and the plurality of grating sensors are configured to detect deformation data of the support rod under an action of resistance at the grasping end. The tracking and navigation system includes an electromagnetic signal transceiving apparatus, the grasping instrument, an ultrasonic detection apparatus, and a navigation display apparatus.

11 Claims, 7 Drawing Sheets

GRASPING INSTRUMENT, TRACKING AND NAVIGATION SYSTEM, METHOD AND DISPLAY APPARATUS, AND STORAGE MEDIUM

CROSS REFERENCE TO RELATED APPLICATION

This patent application claims the benefit and priority of International Application No. PCT/CN2021/076581 filed on Feb. 10, 2021, the disclosure of which is incorporated by reference herein in its entirety as part of the present application.

TECHNICAL FIELD

The present application relates to the technical field of minimally invasive surgical instruments, and in particular to, a grasping instrument, tracking and navigation system, method and display apparatus for bone structure reduction, and a storage medium.

BACKGROUND

Since robot technology was introduced into fracture reduction surgery, many experimental fracture reduction robots have emerged. However, seen from current literature, most experimental fracture reduction robots are used for reduction of a long bone fracture, and there are only a few documents about robots for demonstration of pelvic fracture reduction. In addition, an orthopedic surgical robot is used mostly commonly in such a method that a position-based navigation and guidance system is used to perform positioning matching between the robot and a surgical site, and monitor a relationship therebetween in real time during a surgery to ensure safety of a surgical operation.

In addition, around the pelvis, there are not only a lot of muscles and ligaments, but also abundant tissues such as blood vessels and nerves. Moreover, studies have shown that the injury rate of blood vessels and nerves in pelvic fracture reduction is 0.5%-7.7%. Once injury occurs, serious complications such as shock, dysfunction of defecation and urination and sexual dysfunction easily occur. Therefore, regardless of the surgical operation process of master-slave teleoperation or man-machine physical interaction, a technology based on a force feedback is always noted and explored in a robot-operated surgery. Through force-based monitoring, it is determined whether a force during reduction will cause injuries to tissues such as surrounding ligaments and muscles, so as to prevent secondary injuries during the reduction.

In addition, what means should be adopted to effectively detect a state of tissues such as blood vessels and nerves during pelvic fracture reduction in real time and identify the surgical process is another issue that needs to be solved to achieve high safety operation of pelvic fracture reduction.

SUMMARY

To solve the foregoing technical problems or at least partially solve the foregoing technical problems, the present application provides a grasping instrument, tracking and navigation system, method and display apparatus for bone structure reduction, and a storage medium.

According to a first aspect, the present application provides a grasping instrument for bone structure reduction, including a straight strip-shaped support rod, and a grasping end and a signal end that can be arranged at two ends of the support rod, where the grasping end includes a cutting structure and a grasping structure, and the grasping structure can be arranged between the cutting structure and the support rod; a plurality of grating sensors extending in an axial direction can be arranged on the support rod; the signal end can be provided with an instrument pose feedback sensor for feeding back pose information of the grasping instrument; and the plurality of grating sensors can be configured to detect deformation data of the support rod under an action of resistance at the grasping end.

Optionally, the grasping structure can be a threaded structure; the plurality of grating sensors can be three fiber Bragg grating sensors; the three fiber Bragg grating sensors can be evenly distributed; and the instrument pose feedback sensor can be a cylindrical particle sensor.

According to a second aspect, the present application provides a tracking and navigation system for bone structure reduction, including an electromagnetic signal transceiving apparatus, the above grasping instrument, an ultrasonic detection apparatus, and a navigation display apparatus; the electromagnetic signal transceiving apparatus can be configured to send an electromagnetic signal, and acquire, in a pre-built electromagnetic navigation coordinate system, first pose information of a target bone structure, second pose information of the grasping instrument and third pose information of an ultrasonic probe of the ultrasonic detection apparatus from bone structure pose feedback sensors, the instrument pose feedback sensor and an ultrasonic probe pose feedback sensor, respectively; and send the first pose information, the second pose information and the third pose information to the navigation display apparatus; the ultrasonic detection apparatus can be configured to detect an ultrasonic image of the target bone structure and send the ultrasonic image to the navigation display apparatus; and the navigation display apparatus can be configured to establish a mapping relationship between the ultrasonic image and the electromagnetic navigation coordinate system based on the first pose information, the third pose information and the ultrasonic image, and establish a corresponding relationship between a pose change of the grasping instrument and a displacement change of a to-be-reduced structure in the target bone structure based on the second pose information and the mapping relationship; and reconstruct, in the electromagnetic navigation coordinate system and based on the ultrasonic image, the mapping relationship and the corresponding relationship, a navigation environment for operating the target bone structure; and the grasping end can be configured to grasp the to-be-reduced structure.

Optionally, the grasping instrument can be configured to detect deformation data of a support rod under an action of resistance at the grasping end, and send the deformation data to the navigation display apparatus; and the navigation display apparatus can be further configured to establish a corresponding relationship between the displacement change of the to-be-reduced structure and the resistance based on the deformation data.

Optionally, the bone structure pose feedback sensors can be arranged at a plurality of positions of the target bone structure; the ultrasonic probe pose feedback sensor can be arrange on the ultrasonic probe; and the deformation data includes a displacement change and a rotation angle of the grasping end; and the establishing a corresponding relationship between the displacement change of the to-be-reduced structure and the resistance based on the deformation data includes: simplifying the grasping instrument into a simply supported beam, simplifying a reduction force providing position of the grasping instrument into a base, and simplifying the to-be-reduced structure into resistance applied to a tail end of the simply supported beam; determining the resistance based on displacement change data and the rotation angle of the grasping end; determining change data of the second pose information corresponding to the displacement change; and establishing a corresponding relationship between the displacement change, the change data of the second pose information, and the resistance.

According to a third aspect, the present application provides a tracking and navigation method for bone structure reduction, including: acquiring, from an electromagnetic signal transceiving apparatus, first pose information of a target bone structure, second pose information of a grasping instrument and third pose information of an ultrasonic probe of an ultrasonic detection apparatus in a pre-built electromagnetic navigation coordinate system; acquiring an ultrasonic image of the target bone structure from the ultrasonic detection apparatus; establishing a mapping relationship between the ultrasonic image and the electromagnetic navigation coordinate system based on the first pose information, the third pose information, and the ultrasonic image; establishing a corresponding relationship between a pose change of the grasping instrument and a displacement change of a to-be-reduced structure in the target bone structure based on the second pose information and the mapping relationship; and reconstructing, in the electromagnetic navigation coordinate system and based on the ultrasonic image, the mapping relationship and the corresponding relationship, a navigation environment for operating the target bone structure.

Optionally, the tracking and navigation method further includes: acquiring, from the grasping instrument, deformation data of a support rod of the grasping instrument under an action of resistance at a grasping end of the grasping instrument; and establishing a corresponding relationship between the displacement change of the to-be-reduced structure and the resistance based on the deformation data.

Optionally, the establishing a corresponding relationship between the displacement change of the to-be-reduced structure and the resistance based on the deformation data includes: simplifying the grasping instrument into a simply supported beam, simplifying a reduction force providing position of the grasping instrument into a base, and simplifying the to-be-reduced structure into resistance applied to a tail end of the simply supported beam; determining the resistance based on displacement change data and the rotation angle of the grasping end; determining change data of the second pose information corresponding to the displacement change; and establishing a corresponding relationship between the displacement change, the change data of the second pose information, and the resistance.

According to a fourth aspect, the present application provides a tracking and navigation display apparatus for bone structure reduction, including: a memory, a processor, and a computer program stored on the memory and executable on the processor, where the steps of the tracking and navigation method according to any one of the foregoing implementations can be implemented when the computer program can be executed by the processor.

According to a fifth aspect, the present application provides a computer-readable storage medium, where the computer-readable storage medium stores a tracking and navigation program for bone structure reduction, and the steps of the tracking and navigation method according to any one of the foregoing implementations can be implemented when the tracking and navigation program can be executed by a processor.

Compared with the prior art, the foregoing technical solutions provided in the embodiments of the present application have the following advantages.

According to each embodiment of the present application, the deformation data of the support rod under the action of the resistance at the grasping end can be detected by the grating sensors extending in the axial direction and arranged on the support rod, so that the corresponding relationship between the deformation data of the support rod and the resistance can be effectively established, and then a magnitude of the reduction force applied to the grasping instrument can be determined based on target displacement for reduction during reduction of the bone structure, so as to effectively solve the problem of secondary injury. In addition, through the instrument pose feedback sensor arranged at the signal end and configured to feed back the pose information of the grasping instrument, the corresponding relationship between the pose information change of the grasping instrument and the target displacement of the grasping end can be effectively established, so as to provide navigation planning of the grasping instrument and the reduction force during the reduction of the bone structure.

BRIEF DESCRIPTION OF THE DRAWINGS

The accompanying drawings incorporated into the description and constituting a part of the description illustrate the embodiments of the present disclosure, and can be used together with the description to explain the principles of the present disclosure.

To describe the technical solutions in the embodiments of the present disclosure or in the prior art more clearly, the following briefly describes the accompanying drawings required for the description of the embodiments or the prior art. Apparently, a person of ordinary skill in the art may still derive other accompanying drawings from these accompanying drawings without creative efforts.

Figure 1:
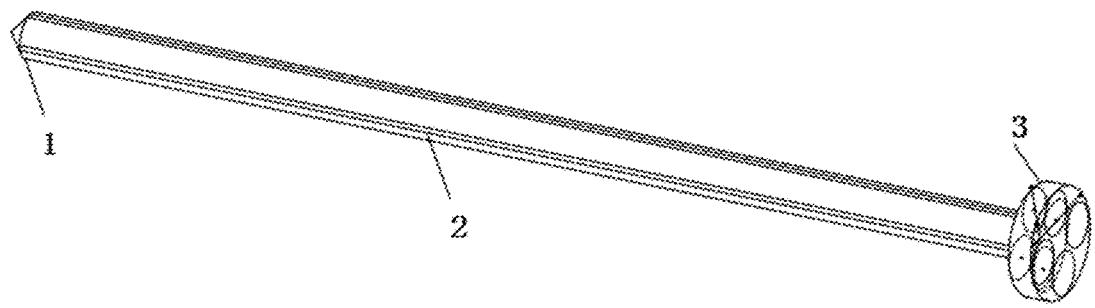
FIG. 1 is a schematic diagram of a grasping instrument according to each embodiment of the present application.

Reference numerals used in the figures: grasping end—1, support rod—2, signal end—3, threaded structure—4, drill bit provided with a cutting edge—5, grasping instrument—6, fiber Bragg grating sensor—7, electromagnetic nail fixed with electromagnetic particles—8, granular electromagnetic sensor—9, electromagnetic signal transceiving apparatus—10, electromagnetic pose signal—11, navigation display apparatus—12, magnetic external characteristic mark—13, grasping instrument of a tissue—instrument interaction module—14, Tail end grasping by robot/operator—15, deformation and stress inforamtion—16, robot/operator—17, ultrasonic information—18, magnetic characteristic structure—19, bone structure—20, ultrasonic probe of ultrasonic detection apparatus —21, magnetic external characteristic mark B—22, ultrasonic image —23, ultrasonic probe support and coordinate systemPref—24, external navigation marker point—25, external state of bone structure —26, internal state of bone structure—27, Resistance moment m—28, and relationship between ultrasonic image coordinate system and ultrasonic probe coordinate system—29.

DETAILED DESCRIPTION

Understandably, the specific embodiments described herein are merely intended to explain the present disclosure but not to limit the present disclosure.

In the following description, the terms such as "module", "component" and "unit" used to represent elements are only for convenience of description of the present disclosure, and have no specific meaning themselves. Thus, "module", "component" and "unit" may be used interchangeably.

Embodiment 1

Figure 2:
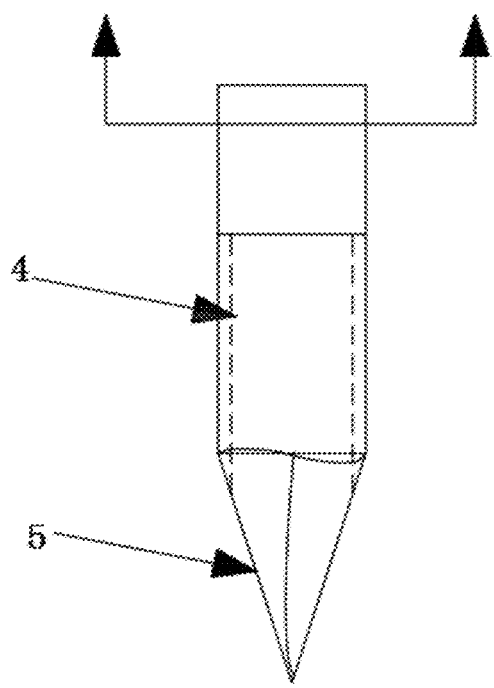
FIG. 2 is a schematic diagram of a grasping end of a grasping instrument according to each embodiment of the present application.
Figure 3:
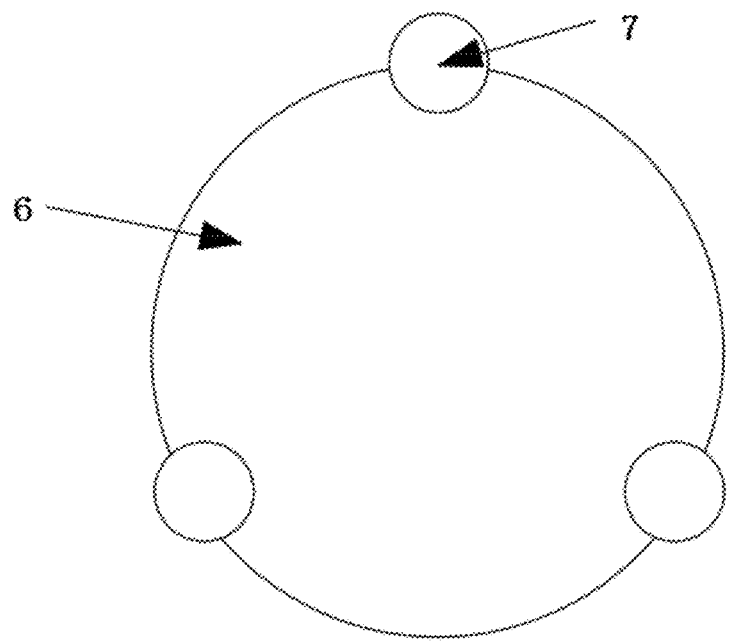
FIG. 3 is a schematic diagram of the grasping instrument shown in FIG. 2.

As shown in FIG. 1 to FIG. 3, this embodiment of the present disclosure provides a grasping instrument 6 for bone structure 20 reduction, including a straight strip-shaped support rod 2, and a grasping end 1 and a signal end 3 that can be arranged at two ends of the support rod 2, where the grasping end 1 includes a cutting structure and a grasping structure, and the grasping structure can be arranged between the cutting structure and the support rod 2; a plurality of grating sensors extending in an axial direction can be arranged on the support rod 2; the signal end 3 can be provided with an instrument pose feedback sensor for feeding back pose information of the grasping instrument 6; and the plurality of grating sensors can be configured to detect deformation data of the support rod 2 under an action of resistance at the grasping end 1.

Optionally, the grasping structure can be a threaded structure 4 and can be a threaded portion of the grasping instrument 6; the plurality of grating sensors can be three fiber Bragg grating sensors 7; the three fiber Bragg grating sensors 7 can be evenly distributed; the instrument pose feedback sensor can be a cylindrical particle sensor, and the cutting structure can be a drill bit 5.

According to this embodiment of the present application, the deformation data of the support rod 2 under the action of the resistance at the grasping end 1 can be detected by the grating sensors extending in the axial direction and arranged on the support rod 2, so that a corresponding relationship between the deformation data of the support rod 2 and the resistance can be effectively established, and then a magnitude of a reduction force applied to the grasping instrument 6 can be determined based on target displacement for reduction during reduction of the bone structure 20, so as to effectively solve the problem of secondary injury. In addition, through the instrument pose feedback sensor arranged at the signal end 3 and configured to feed back the pose information of the grasping instrument 6, the corresponding relationship between the pose information change of the grasping instrument and the target displacement of the grasping end 1 can be effectively established, so as to provide navigation planning of the grasping instrument 6 and the reduction force during the reduction of the bone structure 20.

In detail, FIG. 1 can be a schematic structural diagram of a grasping instrument 6 for bone structure 20 reduction. As shown in FIG. 1, the grasping instrument 6 includes the support rod 2, and the grasping end 1 and the signal end 3 that can be arranged at two ends of the support rod 2 respectively. A tail end of the grasping end 1 can be a sharp drill bit 5; the support rod 2 includes a hard straight strip-shaped rod piece; a plurality of fiber Bragg grating sensors 7 extending in an axial direction can be arranged in the rod piece; the signal end 3 can be provided with an instrument pose feedback sensor, and the sensor can be fixed to the signal end of the rod piece through interference fit. As shown in FIG. 2, a thread can be provided between the drill bit 5 and the rod piece, and the drill bit 5 can be provided with a cutting edge to facilitate entry into the bone structure 20.

As shown in FIG. 3, the fiber Bragg grating sensors 7 can be evenly distributed on a cross-section of the rod piece. In this embodiment of the present disclosure, three or a different number of fiber Bragg grating sensors 7 may be provided. In FIG. 3, it can be seen that the fiber Bragg grating sensor 7 can be placed in a groove after the groove can be formed in an outer surface of the rod piece, and an outer surface part of the fiber Bragg grating sensor 7 protrudes from the rod piece. Considering that the rod piece needs to be manually or mechanically clamped during bone structure 20 reduction, which may lead to damage to the fiber Bragg grating sensor 7, a protective housing needs to be arranged on the surface of the fiber Bragg grating sensor 7, or the fiber Bragg grating sensor 7 may be embedded inside the rod piece. Certainly, it should be understood that the rod piece and the grasping end 1 can be made of medical material, preferably a medical metal, for the purpose of medical hygiene.

Figure 4:
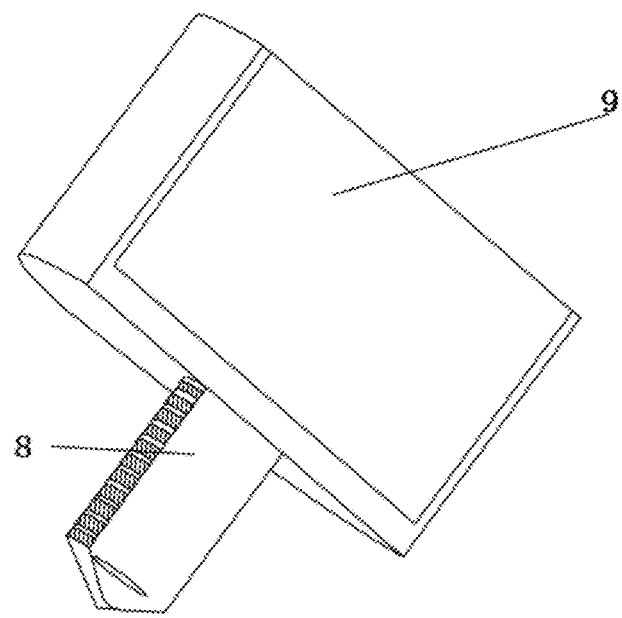
FIG. 4 is a schematic diagram of a cylindrical particle sensor according to each embodiment of the present application.

As shown in FIG. 4, the instrument pose feedback sensor can be a cylindrical particle sensor, which can be a magnetic structure, and may be a cylindrical particle sensor of OMMO Company. The sensor has a diameter of 7.8 mm and a thickness of 4 mm, and can output six-degree-of-freedom pose information. A base of the magnetic structure includes a screw with a drill bit 5 and a rear head for fixing an electromagnetic sensor. By means of six-degree-of-freedom information of the electromagnetic sensor, external surface points of the magnetic structure can be converted into a point set Y in a coordinate system of an electromagnetic navigation system.

Embodiment 2

Figure 5:
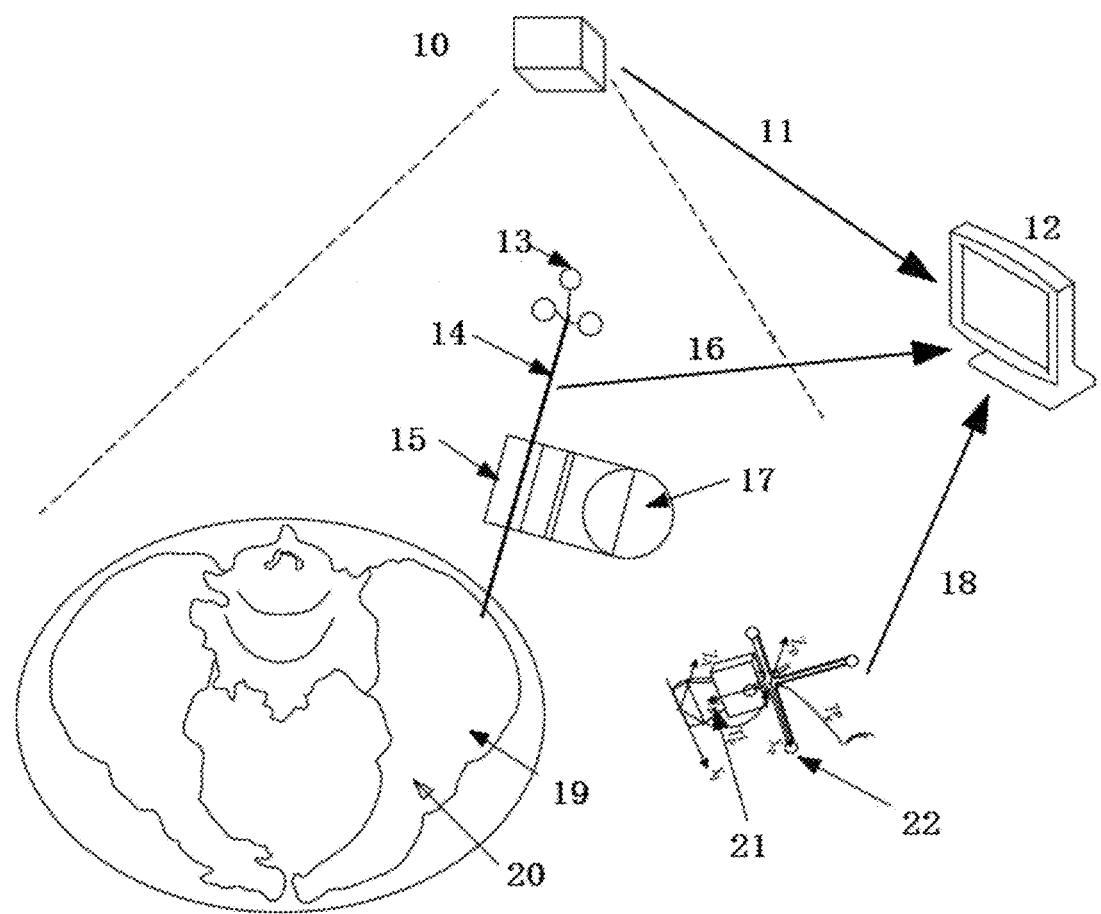
FIG. 5 is a principle diagram of a tracking and navigation system according to each embodiment of the present application.

As shown in FIG. 5, this embodiment of the present disclosure provides a tracking and navigation system for bone structure 20 reduction, including an electromagnetic signal transceiving apparatus 10, the grasping instrument 6 described in Embodiment 1, an ultrasonic detection apparatus, and a navigation display apparatus 12; the electromagnetic signal transceiving apparatus 10 can be configured to send an electromagnetic signal, and acquire, in a pre-built electromagnetic navigation coordinate system, first pose information of a target bone structure, second pose information of the grasping instrument 6 and third pose information of an ultrasonic probe of the ultrasonic detection apparatus from bone structure 20 pose feedback sensors, the instrument pose feedback sensor and an ultrasonic probe 21 pose feedback sensor, respectively; and send the first pose information, the second pose information and the third pose information to the navigation display apparatus 12; the ultrasonic detection apparatus can be configured to detect an ultrasonic image 23 of the target bone structure 20 and send the ultrasonic image 23 to the navigation display apparatus 12; and the navigation display apparatus 12 can be configured to establish a mapping relationship between the ultrasonic image 23 and the electromagnetic navigation coordinate system based on the first pose information, the third pose information and the ultrasonic image, and establish a corresponding relationship between a pose change of the grasping instrument and a displacement change of a to-be-reduced structure in the target bone structure based on the second pose information and the mapping relationship; and reconstruct, in the electromagnetic navigation coordinate system and based on the ultrasonic image 23, the mapping relationship and the corresponding relationship, a navigation environment for operating the target bone structure 20; and the grasping end 1 can be configured to grasp the to-be-reduced structure. The bone structure 20 pose feedback sensors can be arranged at a plurality of positions of the target bone structure 20; and the ultrasonic probe 21 pose feedback sensor can be arranged on the ultrasonic probe 21. The bone structure 20 pose feedback sensors and the ultrasonic probe 21 pose feedback sensor can be cylindrical particle sensors, which can be magnetic structures, and may be cylindrical particle sensors of OMMO Company. The sensors each have a diameter of 7.8 mm and a thickness of 4 mm, and can output six-degree-of-freedom pose information. A base of the magnetic structure includes a screw with a drill bit 5 and a rear head for fixing an electromagnetic sensor. By means of six-degree-of-freedom information of the electromagnetic sensor, external surface points of the magnetic structure can be converted into a point set Y in a coordinate system of an electromagnetic navigation system.

In this embodiment of the present disclosure, the ultrasonic probe 21 of the ultrasonic probe 21 pose feedback sensor tests external structural information of the bone structure 20, and an operation navigation environment can be reconstructed based on the pose information of the bone structure 20 pose feedback sensor, so as to accurately reflect the pose information of the bone structure 20 in real time, thereby providing an accurate operation environment by effectively combining a real-time ultrasonic image.

The bone structure 20 pose feedback sensors can be magnetic characteristic structures 19, the instrument pose feedback sensor can be an external marking point A, and the ultrasonic probe 21 pose feedback sensor can be a magnetic mark B. That is, the magnetic characteristic structures 19 can be fixed at a plurality of positions of a to-be-reduced target bone structure 20 respectively, the grasping instrument 6 grasps and fixes a to-be-reduced structure of the target bone structure 20, and the electromagnetic signal transceiving apparatus 10 collects position information of the magnetic characteristic structures 19, obtains an internal pose state of the target bone structure 20, and collects external pose characteristics of the external marking point A of the grasping instrument 6; the grasping instrument 6 senses its own stress deformation data in real time, and represents a stress state of the bone structure 20; the ultrasonic probe can be provided with the magnetic mark B, and the ultrasonic probe 21 collects the external structural information of the bone structure 20 and the information of the magnetic characteristic structures 19, reconstructs a shape and pose of the bone structure 20, determines the positions of the magnetic structures, and converts the information into a tracking coordinate system by means of a magnetic mark.

In detail, as shown in FIG. 5, the tracking and navigation system for bone structure 20 reduction can be an apparatus for accurately identifying/tracking a pose/stress state of the bone structure 20 in a closed environment, and includes an electromagnetic signal transceiving apparatus 10, an ultrasonic detection apparatus, magnetic characteristic structures 19, magnetic external characteristic marks, a tissue-instrument interaction module, and a navigation display apparatus 12. The tissue-instrument interaction module includes a grasping instrument 6, fiber Bragg grating sensors 7 distributed on the grasping instrument, the magnetic external characteristic marks, and a photodetector for detecting information of the fiber Bragg grating sensors 7. The fiber Bragg grating sensors 7 can be connected to a fiber detector through fiber interfaces, and the fiber interfaces can be arranged on the bone structure 20 grasping instrument 6 and can be in communication connection with the fiber detector by means of a wired cable or a wireless module.

The granular magnetic characteristic structures 19 can be solidified on a to-be-identified and to-be-tracked bone structure 20, to form internal characteristic points. One end of the grasping instrument 6 grasps and fixes the to-be-identified, to-be-tracked and to-be-reduced structure, and the other end can be provided with a magnetic external characteristic mark A13. The ultrasonic probe 21 can be provided with a magnetic external characteristic mark B22. A working area of the electromagnetic signal transceiving apparatus 10 covers an active area of the to-be-tracked bone structure. Relevant information can be transmitted to a navigation display platform for display. The ultrasonic probe 21 with the magnetic mark B collects geometric shape information of the bone structure 20 and converts the information to an electromagnetic signal sending and tracking platform coordinate system, so as to reconstruct a navigation environment for operation of the bone structure 20.

Figure 7:
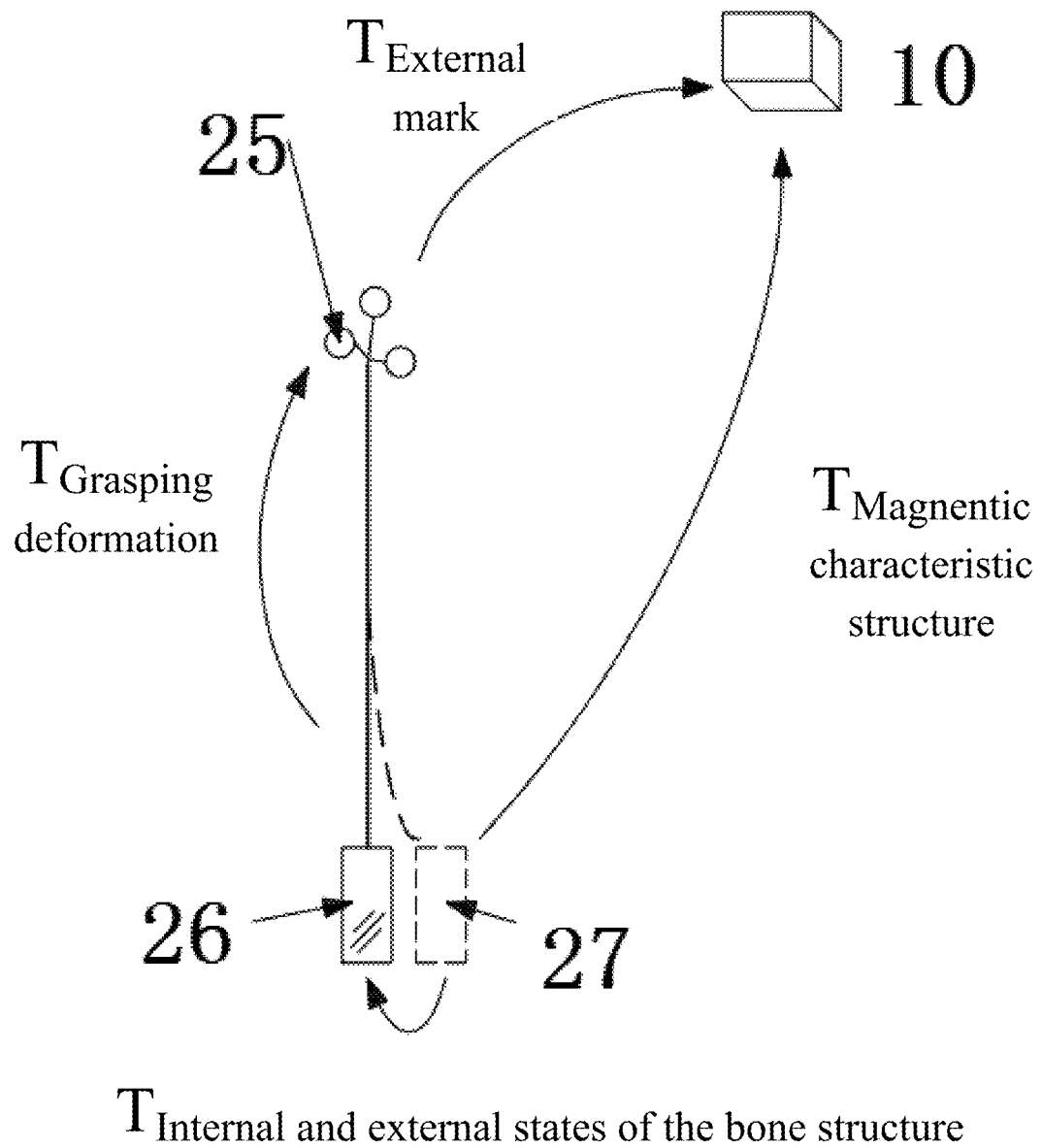
FIG. 7 is a schematic diagram of electromagnetic information collection of a tracking and navigation system according to each embodiment of the present application.

FIG. 7 can be a schematic diagram of collection of information based on an electromagnetic signal in a tracking and navigation system for bone structure 20 reduction by using a tracking and navigation method for bone structure 20 reduction. As shown in FIG. 7, during bone structure 20 reduction, magnetic characteristic structures 19 can be installed on the to-be-reduced structure under the skin, and can be characteristic points under the skin (i.e., internal characteristic points), while marks for assisting in identifying a robot, grasping a steel needle and the ultrasonic probe 21 can be external marking points. Steps can be as follows:

First step: Continuously collect ultrasonic images 23 including internal characteristic points, record a position of an ultrasonic probe 21 pose feedback sensor at a time of collecting each image, i.e., a position of an external characteristic point B, and restore pose data of the ultrasonic probe 21 based on this position.

Figure 6:
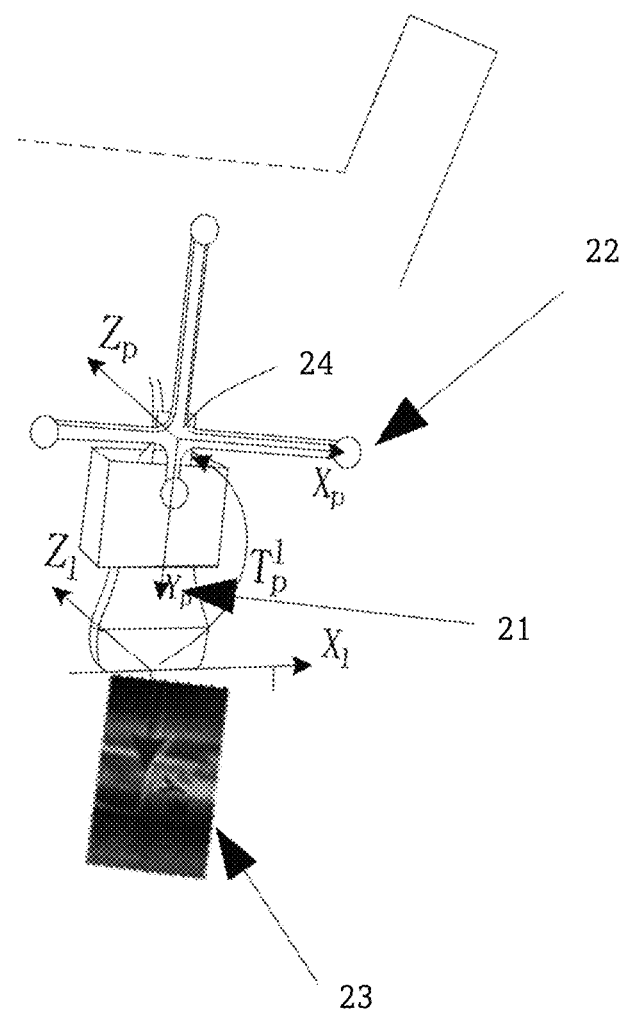
FIG. 6 is a schematic diagram of a relationship between an ultrasonic image coordinate system and an ultrasonic probe coordinate system of a tracking and navigation system according to each embodiment of the present application.

As shown in FIG. 6, any point, $P_{img}$, in the ultrasonic image 23 can be converted into a point coordinate $P_{ref}$ in an ultrasonic probe 21 (reference frame) coordinate system, which meets a relationship in the following formula:

$$p_{ref} = T_p^I \times p_{img}$$

$T_p^I$ can be a conversion matrix between an ultrasonic image 23 coordinate system and an ultrasonic probe 21 coordinate system. When an ultrasonic probe 21 reference frame and the ultrasonic probe 21 can be fixed, the conversion matrix can be determined and can be obtained by calibration.

Second step: Extract characteristic points of an ultrasonic image 23 sequence, and obtain, by using the foregoing formula, a three-dimensional (3D) point coordinate set X including magnetic characteristic structures 19 under the ultrasonic probe 21, so as to implement reconstruction of an ultrasonic point set.

Third step: Calculate three-dimensional coordinates of matched characteristic points under the ultrasonic probe 21 by combining pose data of the ultrasonic probe 21, so as to implement reconstruction of the ultrasonic point set.

Figure 9:
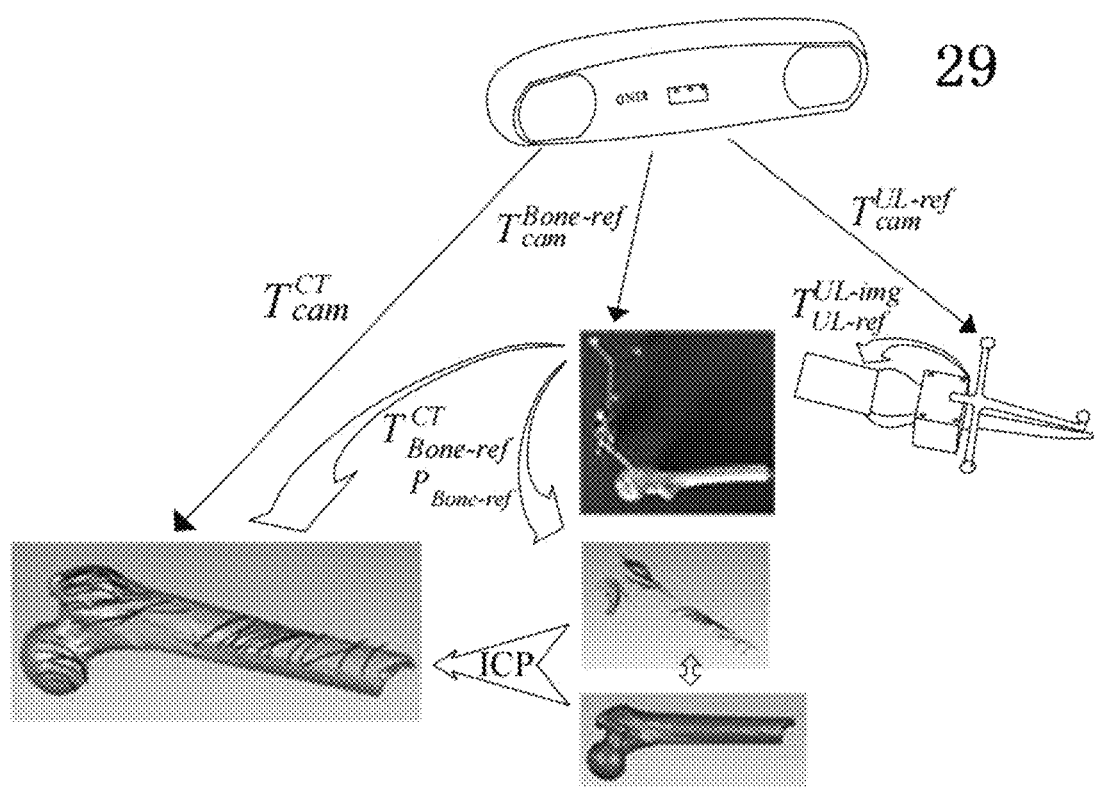
FIG. 9 is a schematic diagram of path planning based on a stress state of a tracking and navigation system according to each embodiment of the present application.

Fourth step: Solve a mapping relationship between an electromagnetic navigation space and an ultrasonic image 23 space by using the three-dimensional point coordinate set X under the ultrasonic probe 21 and a point set Y of external surface points of the magnetic structures in an electromagnetic navigation system coordinate system:

calculate average values $$\bar{x} = \frac{1}{n}\sum_{i=1}^{n} x_i \text{ and } \bar{y} = \frac{1}{n}\sum_{i=1}^{n} y_i$$

of the point sets X and Y, where $\bar{X}=(x_1-\bar{x}, \ldots, x_i-\bar{x}, \ldots, x_n-\bar{x})$, $\bar{Y}=(y_1-\bar{y}, \ldots, y_i-\bar{y}, \ldots, y_n-\bar{y})$, and $M=\bar{Y}\bar{X}^T$; perform singular value decomposition (SVD) on M; $M=UDV^T$; and then represent a determinant of $UV^T$ by using $Det(UV^T)$ where it can be defined that $$S = \begin{pmatrix} 1 & 0 & 0 \\ 0 & 1 & 0 \\ 0 & 0 & Det(UV^T) \end{pmatrix}$$

it can be defined that $$R = UV^T, t = \bar{y} - R\bar{x}, \begin{bmatrix} R & t \\ 0 & 1 \end{bmatrix}$$

represents a pose matrix of the ultrasonic image 23 coordinate system in the electromagnetic navigation system coordinate system, i.e., a mapping relationship between the ultrasonic image 23 and the navigation space ($T_{cam}^{UL-ref}$ in FIG. 9).

Fifth step: Perform three-dimensional reconstruction (such as Marching Cube) on preoperative (before reduction) computed tomography (CT) data, and convert the preoperative CT data into 3D model data.

Sixth step: Rigidly register preoperative model data with reconstructed ultrasonic point set data (for example, by using an iterative closest point (ICP) algorithm), so as to obtain a mapping relationship between a preoperative CT image space and an intraoperative ultrasonic image 23.

So far, a mapping relationship between the preoperative CT image space, the intraoperative ultrasonic image 23 space and the electromagnetic navigation space has been established.

In some implementations, the grasping instrument 6 can be configured to detect deformation data of a support rod 2 under an action of resistance at the grasping end 1, and send the deformation data to the navigation display apparatus 12; and the navigation display apparatus 12 can be further configured to establish a corresponding relationship between the displacement change of the to-be-reduced structure and the resistance based on the deformation data.

The deformation data includes a displacement change and a rotation angle of the grasping end 1.

Optionally, the establishing a corresponding relationship between the displacement change of the to-be-reduced structure and the resistance based on the deformation data includes: simplifying the grasping instrument 6 into a simply supported beam, simplifying a reduction force providing position of the grasping instrument 6 into a base, and simplifying the to-be-reduced structure into resistance applied to a tail end of the simply supported beam; determining the resistance based on displacement change data and the rotation angle of the grasping end 1; determining change data of the second pose information corresponding to the displacement change; and establishing a corresponding relationship between the displacement change, the change data of the second pose information, and the resistance.

Figure 8:
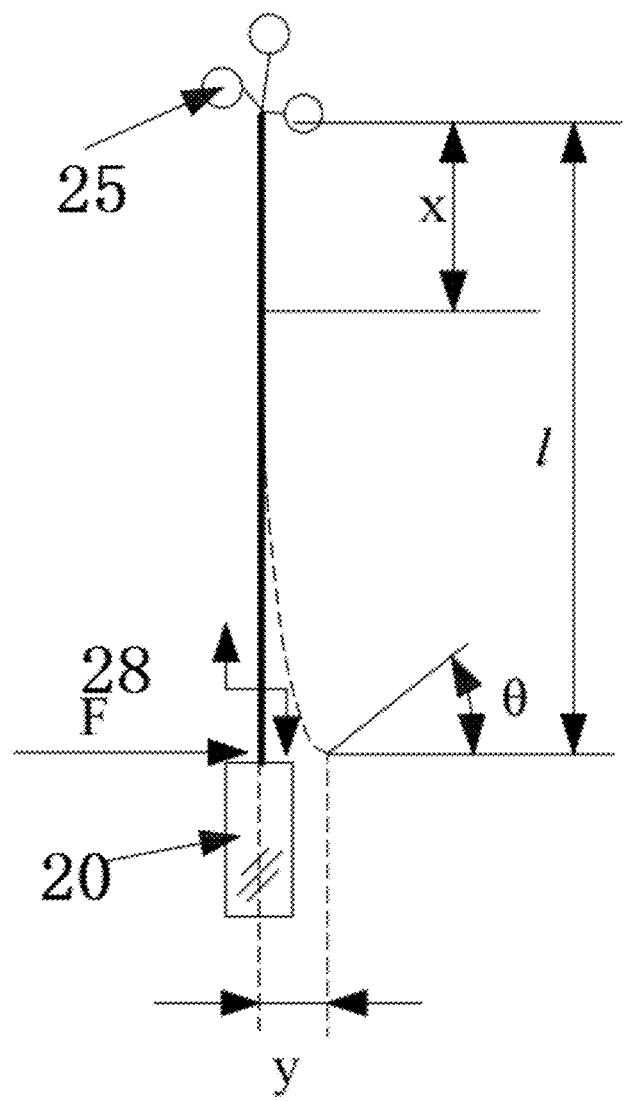
FIG. 8 is a schematic diagram of a deformation state of a grasping instrument according to each embodiment of the present application.

In detail, FIG. 8 can be a schematic diagram of a deformation state of a grasping instrument in an implementation solution of a tracking and navigation system for bone structure 20 reduction according to an embodiment of the present disclosure. The grasping instrument 6 can be simplified into a simply supported beam, a joint of an operator/robot and the grasping instrument 6 (i.e., a reduction force providing position of the grasping instrument 6) can be simplified into a base, and the bone structure 20 can be simplified into resistance (F) and a moment (m) load applied to a tail end of the simply supported beam, to establish a steel needle deformation model.

A rotation angle equation can be established:

$$EI\frac{dy}{dx} = EI\theta = \frac{1}{2}F(x-l)^2 + mx + C$$

A deflection equation can be established:

$$EIy = \frac{1}{6}F(x-l)^3 + \frac{1}{2}mx^2 + Cx + D$$

where E, I, C and D can be constants related to a material and structure of the grasping instrument 6, E can be an elastic modulus of a grasping instrument; I can be a cross-sectional moment of inertia of the grasping instrument; and C and D can be constants, and may be obtained by calibrating the grasping instrument. By detecting deformation quantities y and θ of the grasping instrument by means of fiber Bragg grating sensors 7, the resistance F and moment m of resistance at the tail end can be calculated.

FIG. 9 can be a schematic diagram of a path planning process based on a pose and stress state of a bone structure 20 in an implementation solution of a tracking and navigation system for bone structure 20 reduction according to an embodiment of the present disclosure. As shown in FIG. 9, a grasping instrument 14 of a tissue-instrument interaction module includes a group of rod pieces with a certain geometric shape, a drill bit 5 can be distributed at one end of each of the rod pieces, and a periphery of the drill bit 5 can be provided with a thread. Three (or a plurality of) fiber Bragg grating sensors can be evenly distributed on circumferences of the rod pieces in an axial direction. The other end of the rod piece can be provided with an external characteristic mark A13. The rod piece can be made of a medical metal. One end of the drill bit 5 of the grasping instrument 6 can be implanted into the bone structure 20 and grasps a to-be-reduced structure (broken bone), and the other end can be provided with a magnetic external characteristic mark A13. The operator or the robot operates the to-be-reduced structure by means of the grasping instrument to drive the bone structure 20 to overcome resistance of peripheral soft tissues and move to a position planned by the operator. The three fiber Bragg grating sensors 7 detect the deformation and stress state of the bone structure 20 grasping instrument 6. The external marking point A represents a pose state of the bone structure 20 grasping instrument 6.

An ultrasonic data point set can be reconstructed, and a mapping relationship between a preoperative CT image space, an intraoperative ultrasonic image 23 space and an electromagnetic navigation space can be obtained.

Real-time pose information of the bone structure 20, that is, a grasping pose state of the bone structure 20, can be obtained by monitoring positions of internal characteristic points (magnetic characteristic structures 9) in real time during a surgery and by using the mapping relationship between the preoperative CT image space and the electromagnetic navigation space.

Given the pose of the external marking point A, the deformation data of the grasping rod pieces and poses of the magnetic characteristic structures 19, the bone structure may be regarded as a rigid body without an external force, and a relative pose does not change.

As shown in FIG. 7, an external state of the bone structure 20 can be calculated by means of the external marking point A and a rigid body model.

During reduction, due to the action of soft tissues such as skin and muscles, and a possible side-slip force of the bone structure 20 on the grasping instrument, the positions of internal characteristic points change, which will then lead to deformation of the grasping rod pieces and changes of relative poses of the external marking point A and the bone structure 20.

As shown in FIG. 7, the position of the bone structure 20 monitored by the magnetic characteristic structures 19 can be an internal state of the bone structure 20.

A relationship between internal and external poses represents a change in the number of relative positions of the grasping instrument 6 and the solidified bone structure 20. A relationship between operators can be more accurately sensed. A stress state between bone structures 20 can be corrected.

The stress state of the bone structures 20 can be analyzed by combining the internal and external states of the bone structures 20. A stress-deformation model of the pose of the external marking point A, the deformation data of the grasping rod pieces and the magnetic characteristic structures 19 can be established. The stress of the bone structure 20 and the grasping rod pieces can be analyzed by means of their relative positions.

In this embodiment of the present disclosure, the operator or the robot operates the to-be-reduced structure by means of the grasping instrument to drive the to-be-reduced structure to overcome resistance of peripheral soft tissues and move to a position planned by the operator. The three fiber Bragg grating sensors 7 detect the deformation and stress state of the bone structure 20 grasping instrument 6. The external marking point A represents a pose state of the bone structure 20 grasping instrument 6.

The ultrasonic probe 21 with the magnetic mark B tests external structural information of the bone structure 20 and pose information of the magnetic characteristic structures 19, and an operation navigation environment can be reconstructed based on the pose information of the bone structure pose feedback sensor, so as to accurately reflect the pose information of the bone structure 20 in real time, thereby providing an accurate operation environment by effectively combining a real-time ultrasonic image.

In addition, according to the present disclosure, the magnetic characteristic structures 19 can be solidified on the bone structure 20, so that the pose information of the bone structure 20 can be converted into an electromagnetic signal sending and tracking platform coordinate system by means of an electromagnetic signal sending and tracking platform, to represent pose state information of the bone structure 20 in vivo. Then pose state information of the grasping instrument 6 and the bone structure 20 can be represented by using the external information with the magnetic mark A, the pose information of the magnetic characteristic structures 19, and the deformation data of the grasping rod pieces.

Embodiment 3

This embodiment of the present disclosure provides a tracking and navigation method for bone structure 20 reduction, including: acquiring, from an electromagnetic signal transceiving apparatus 10, first pose information of a target bone structure 20, second pose information of a grasping instrument 6 and third pose information of an ultrasonic probe 21 of an ultrasonic detection apparatus in a pre-built electromagnetic navigation coordinate system; acquiring an ultrasonic image 23 of the target bone structure 20 from the ultrasonic detection apparatus; establishing a mapping relationship between the ultrasonic image 23 and the electromagnetic navigation coordinate system based on the first pose information, the third pose information, and the ultrasonic image 23; establishing a corresponding relationship between a pose change of the grasping instrument 6 and a displacement change of a to-be-reduced structure in the target bone 20 structure based on the second pose information and the mapping relationship; and reconstructing, in the electromagnetic navigation coordinate system and based on the ultrasonic image 23, the mapping relationship and the corresponding relationship, a navigation environment for operating the target bone structure 20.

In some implementations, the tracking and navigation method further includes: acquiring, from the grasping instrument 6, deformation data of a support rod 2 of the grasping instrument 6 under an action of resistance at a grasping end 1 of the grasping instrument 6; and establishing a corresponding relationship between the displacement change of the to-be-reduced structure and the resistance based on the deformation data.

Optionally, the establishing a corresponding relationship between the displacement change of the to-be-reduced structure and the resistance based on the deformation data includes: simplifying the grasping instrument into a simply supported beam, simplifying a reduction force providing position of the grasping instrument 6 into a base, and simplifying the to-be-reduced structure into resistance applied to a tail end of the simply supported beam; determining the resistance based on displacement change data and the rotation angle of the grasping end 1; determining change data of the second pose information corresponding to the displacement change; and establishing a corresponding relationship between the displacement change, the change data of the second pose information, and the resistance.

Embodiment 4

This embodiment of the present disclosure provides a tracking and navigation display apparatus 12 for bone structure reduction, including: a memory, a processor, and a computer program stored on the memory and executable on the processor, where the steps of the tracking and navigation method according to any one of the implementations of Embodiment 3 can be implemented when the computer program can be executed by the processor.

Embodiment 5

This embodiment of the present disclosure provides a computer-readable storage medium, where the computer-readable storage medium stores a tracking and navigation program for bone structure 20 reduction, and the steps of the tracking and navigation method according to any one of the implementations of Embodiment 3 can be implemented when the tracking and navigation program can be executed by a processor.

In the specific implementation process, for Embodiment 3-5, reference may be made to Embodiments 1 and 2, which have corresponding technical effects.

It should be noted that terms "including", "comprising" or any other variants thereof can be intended to cover non-exclusive inclusion, so that a process, method, article or apparatus including a series of elements includes not only those elements but also other elements not explicitly listed, or elements inherent to such a process, method, article, or apparatus. Without further limitation, an element qualified by the phrase "including a . . . " does not exclude the presence of an additional identical element in the process, method, article, or device including the element.

The serial numbers of the embodiments of the present disclosure can be merely for description and do not represent a preference of the embodiments.

By means of the foregoing description of the implementations, a person skilled in the art can clearly understand that the foregoing method in the embodiments may be implemented by means of software and a necessary general-purpose hardware platform. Certainly, hardware may be used, but the former can be a better implementation in many cases. Based on this understanding, the technical solution of the present disclosure essentially, or a part contributing to the prior art, may be embodied in a form of a software product. The computer software product can be stored on a storage medium (such as a read only memory (ROM)/random access memory (RAM), a magnetic disk, and a compact disc), and includes a plurality of instructions to enable a terminal (which may be a mobile phone, a computer, a server, an air-conditioner, a network device, or the like) to perform the method according to each embodiment of the present disclosure.

The embodiments of the present disclosure have been described above with reference to the accompanying drawings, but the present disclosure can be not limited to the foregoing specific implementations. The foregoing specific implementations can be only illustrative and not restrictive. Under the inspiration of the present disclosure, a person of ordinary skill in the art can make many improvements without departing from the purpose of the present disclosure and the protection scope defined by the claims, and these improvements shall fall within the protection scope of the present disclosure.

What is claimed is:

1. A grasping instrument for bone structure reduction, comprising a straight strip-shaped support rod, and a grasping end and a signal end that are arranged at two ends of the support rod, wherein the grasping end comprises a cutting structure and a grasping structure, and the grasping structure is arranged between the cutting structure and the support rod; a plurality of grating sensors extending in an axial direction are arranged on the support rod; the signal end is provided with an instrument pose feedback sensor for feeding back pose information of the grasping instrument; and the plurality of grating sensors are configured to detect deformation data of the support rod under an action of resistance at the grasping end.

2. The grasping instrument for bone structure reduction of claim 1, wherein the grasping structure is a threaded structure; the plurality of grating sensors are three fiber Bragg grating sensors; the three fiber Bragg grating sensors are evenly distributed; and the instrument pose feedback sensor is a cylindrical particle sensor.

3. A tracking and navigation system for bone structure reduction, comprising an electromagnetic signal transceiving apparatus, the grasping instrument of claim 1, an ultrasonic detection apparatus, and a navigation display apparatus; wherein the electromagnetic signal transceiving apparatus is configured to send an electromagnetic signal, and acquire, in a pre-built electromagnetic navigation coordinate system, first pose information of a target bone structure, second pose information of the grasping instrument and third pose information of an ultrasonic probe of the ultrasonic detection apparatus from bone structure pose feedback sensors, the instrument pose feedback sensor and an ultrasonic probe pose feedback sensor, respectively; and send the first pose information, the second pose information and the third pose information to the navigation display apparatus;

the ultrasonic detection apparatus is configured to detect an ultrasonic image of the target bone structure and send the ultrasonic image to the navigation display apparatus; and the navigation display apparatus is configured to establish a mapping relationship between the ultrasonic image and the electromagnetic navigation coordinate system based on the first pose information, the third pose information and the ultrasonic image, and establish a corresponding relationship between a pose change of the grasping instrument and a displacement change of a to-be-reduced structure in the target bone structure based on the second pose information and the mapping relationship; and reconstruct, in the electromagnetic navigation coordinate system and based on the ultrasonic image, the mapping relationship and the corresponding relationship, a navigation environment for operating the target bone structure; and the grasping end is configured to grasp the to-be-reduced structure.

4. The tracking and navigation system of claim 3, wherein the grasping instrument is configured to detect deformation data of a support rod under an action of resistance at the grasping end, and send the deformation data to the navigation display apparatus; and the navigation display apparatus is further configured to establish a corresponding relationship between the displacement change of the to-be-reduced structure and the resistance based on the deformation data.

5. The tracking and navigation system of claim 3, wherein the bone structure pose feedback sensors are arranged at a plurality of positions of the target bone structure; the ultrasonic probe pose feedback sensor is arrange on the ultrasonic probe; and the deformation data comprises a displacement change and a rotation angle of the grasping end; and the establishing a corresponding relationship between the displacement change of the to-be-reduced structure and the resistance based on the deformation data comprises:

simplifying the grasping instrument into a simply supported beam, simplifying a reduction force providing position of the grasping instrument into a base, and simplifying the to-be-reduced structure into resistance applied to a tail end of the simply supported beam;

determining the resistance based on displacement change data and the rotation angle of the grasping end;

determining change data of the second pose information corresponding to the displacement change; and establishing a corresponding relationship between the displacement change, the change data of the second pose information, and the resistance.

6. A tracking and navigation method for bone structure reduction, comprising:

acquiring, from an electromagnetic signal transceiving apparatus, first pose information of a target bone structure, second pose information of a grasping instrument and third pose information of an ultrasonic probe of an ultrasonic detection apparatus in a pre-built electromagnetic navigation coordinate system;

acquiring an ultrasonic image of the target bone structure from the ultrasonic detection apparatus;

establishing a mapping relationship between the ultrasonic image and the electromagnetic navigation coordinate system based on the first pose information, the third pose information, and the ultrasonic image;

establishing a corresponding relationship between a pose change of the grasping instrument and a displacement change of a to-be-reduced structure in the target bone structure based on the second pose information and the mapping relationship; and reconstructing, in the electromagnetic navigation coordinate system and based on the ultrasonic image, the mapping relationship and the corresponding relationship, a navigation environment for operating the target bone structure.

7. The tracking and navigation method of claim 6, further comprising:

acquiring, from the grasping instrument, deformation data of a support rod of the grasping instrument under an action of resistance at a grasping end of the grasping instrument; and establishing a corresponding relationship between the displacement change of the to-be-reduced structure and the resistance based on the deformation data.

8. The tracking and navigation method of claim 6, wherein the establishing a corresponding relationship between the displacement change of the to-be-reduced structure and the resistance based on the deformation data comprises:

simplifying the grasping instrument into a simply supported beam, simplifying a reduction force providing position of the grasping instrument into a base, and simplifying the to-be-reduced structure into resistance applied to a tail end of the simply supported beam;

determining the resistance based on displacement change data and the rotation angle of the grasping end;

determining change data of the second pose information corresponding to the displacement change; and establishing a corresponding relationship between the displacement change, the change data of the second pose information, and the resistance.

9. The tracking and navigation system of claim 3, wherein the grasping structure is a threaded structure; the plurality of grating sensors are three fiber Bragg grating sensors; the three fiber Bragg grating sensors are evenly distributed; and the instrument pose feedback sensor is a cylindrical particle sensor.

10. The tracking and navigation system according to claim 9, wherein the grasping instrument is configured to detect deformation data of a support rod under an action of resistance at the grasping end, and send the deformation data to the navigation display apparatus; and the navigation display apparatus is further configured to establish a corresponding relationship between the displacement change of the to-be-reduced structure and the resistance based on the deformation data.

11. The tracking and navigation system according to claim 9, wherein the bone structure pose feedback sensors are arranged at a plurality of positions of the target bone structure; the ultrasonic probe pose feedback sensor is arrange on the ultrasonic probe; and the deformation data comprises a displacement change and a rotation angle of the grasping end; and the establishing a corresponding relationship between the displacement change of the to-be-reduced structure and the resistance based on the deformation data comprises:

simplifying the grasping instrument into a simply supported beam, simplifying a reduction force providing position of the grasping instrument into a base, and simplifying the to-be-reduced structure into resistance applied to a tail end of the simply supported beam;

determining the resistance based on displacement change data and the rotation angle of the grasping end;

determining change data of the second pose information corresponding to the displacement change; and establishing a corresponding relationship between the displacement change, the change data of the second pose information, and the resistance.

* * * * *